(12) United States Patent
Piancastelli

(10) Patent No.: US 9,872,929 B2
(45) Date of Patent: Jan. 23, 2018

(54) APPARATUS FOR FRACTIONATION AND INFUSION OF RADIOPHARMACEUTICAL PRODUCTS

(71) Applicant: TEMA SINERGIE S.P.A., Faenza-Ravenna (IT)

(72) Inventor: Luciano Piancastelli, Castelbolognese-Ravenna (IT)

(73) Assignee: TEMA SINERGIE S.P.A., Faenza-Ravenna (IT)

( * ) Notice: Subject to any disclaimer, the term of this patent is extended or adjusted under 35 U.S.C. 154(b) by 332 days.

(21) Appl. No.: 14/351,230

(22) PCT Filed: Oct. 11, 2012

(86) PCT No.: PCT/IT2012/000313
§ 371 (c)(1),
(2) Date: Apr. 11, 2014

(87) PCT Pub. No.: WO2013/054368
PCT Pub. Date: Apr. 18, 2013

(65) Prior Publication Data
US 2014/0249350 A1    Sep. 4, 2014

(30) Foreign Application Priority Data
Oct. 13, 2011 (IT) ................ FI2011A0222

(51) Int. Cl.
*A61K 51/12* (2006.01)
*A61N 5/10* (2006.01)
(Continued)

(52) U.S. Cl.
CPC .......... *A61K 51/121* (2013.01); *A61M 5/142* (2013.01); *A61M 5/14232* (2013.01);
(Continued)

(58) Field of Classification Search
CPC .... A61M 5/142; A61M 5/162; A61M 5/1782; A61M 5/1785; A61M 2039/0027;
(Continued)

(56) References Cited

U.S. PATENT DOCUMENTS 7,905,258 B2    3/2011   Bedeschi
2009/0032729 A1 *  2/2009   Piancastelli ......... A61M 5/1782
                                                250/432 R

FOREIGN PATENT DOCUMENTS

EP    1 860 028        11/2007
EP    1860028 A1 *    11/2007   ............ B65B 3/003
(Continued)

OTHER PUBLICATIONS

International Search Report dated Mar. 22, 2013, corresponding to PCT/IT2012/000313.

*Primary Examiner* — Christine H Matthews
*Assistant Examiner* — Joshua D Lannu
(74) *Attorney, Agent, or Firm* — Young & Thompson

(57) ABSTRACT

Apparatus for fractionation and infusion of radiopharmaceuticals, including a fractionation unit for fractionation into a number of calibrated doses of an amount of radioactive liquid contained in a multidose vial, and a unit for transferring the doses from the fractionation unit to a device for administration thereof to a patient, and further including a controlled-atmosphere ventilated chamber containing the unit for transfer of the doses and the connections to a line for connection to the administering device.

19 Claims, 14 Drawing Sheets

(51) Int. Cl.
*A61M 5/158* (2006.01)
*A61M 5/142* (2006.01)
*A61M 5/168* (2006.01)
*A61M 5/178* (2006.01)
*B65B 3/00* (2006.01)
*A61M 5/162* (2006.01)
*A61M 39/00* (2006.01)

(52) U.S. Cl.
CPC ........ *A61M 5/158* (2013.01); *A61M 5/16831* (2013.01); *A61M 5/1782* (2013.01); *A61M 5/1785* (2013.01); *A61N 5/1001* (2013.01); *B65B 3/003* (2013.01); *A61M 5/162* (2013.01); *A61M 2039/0027* (2013.01); *A61M 2202/049* (2013.01); *A61N 2005/1094* (2013.01)

(58) Field of Classification Search
CPC ........ A61M 2202/049; A61M 5/14232; A61M 5/158; A61M 5/16831; A61K 51/121; A61N 5/1001; A61N 2005/1094
See application file for complete search history.

(56) References Cited

FOREIGN PATENT DOCUMENTS

| EP | 2 179 758 | 4/2010 | |
| EP | 2179758 A2 * | 4/2010 | .......... A61M 5/1785 |
| WO | 99/63547 | 12/1999 | |
| WO | WO 9963547 A2 * | 12/1999 | ............ C07B 59/00 |
| WO | 2008/037939 | 4/2008 | |
| WO | WO 2008037939 A2 * | 4/2008 | .......... A61M 5/1452 |
| WO | 2009/152320 | 12/2009 | |

\* cited by examiner

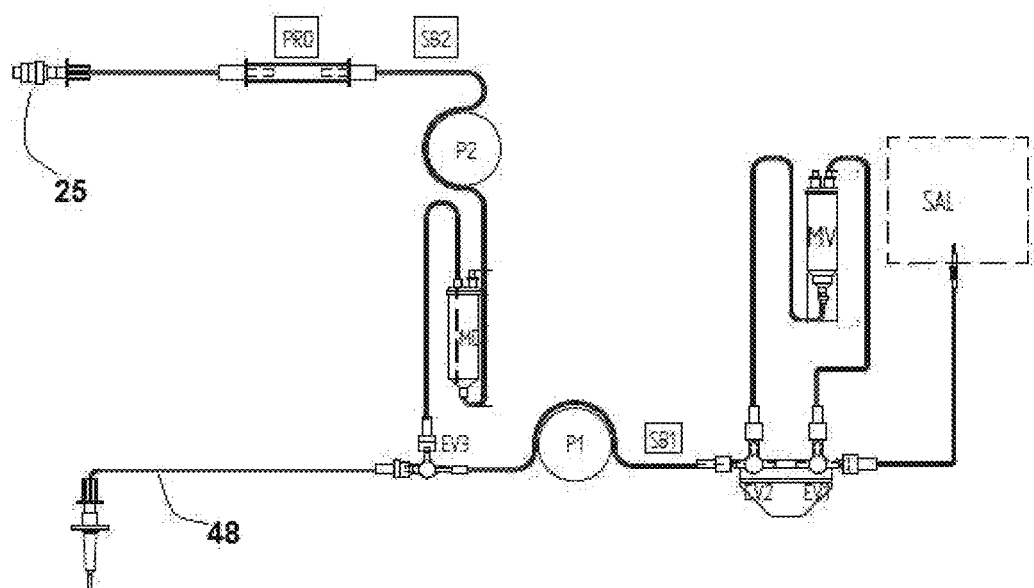
FIG.16a
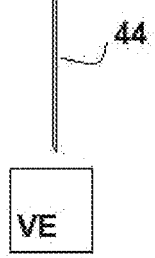
FIG.17
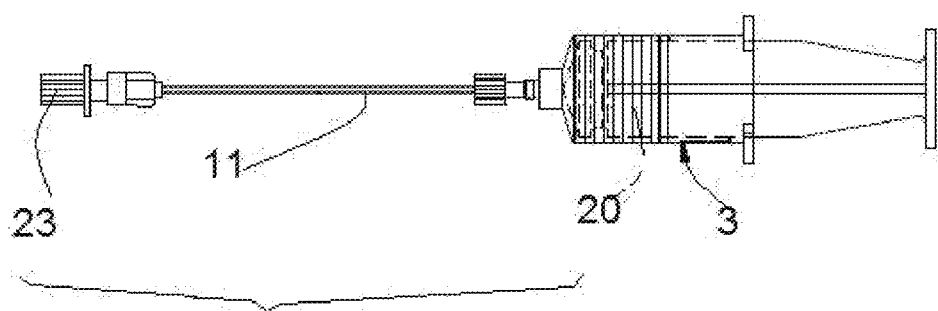

APPARATUS FOR FRACTIONATION AND INFUSION OF RADIOPHARMACEUTICAL PRODUCTS

TECHNICAL SECTOR OF THE INVENTION

The invention relates to an automatic apparatus for fractionation and infusion of radiopharmaceuticals.

PRIOR ART

Known to the current state of the art are apparatuses available on the market known as fractionators, which distribute the radioactive liquid contained in a multidose vial into a number of single-dose vials or syringes for various patients.

The personal dose thus fractionated can then be administered to the patient by means of devices referred to as infusers.

There moreover exist systems that integrate fractionation of the multidose vial and infusion of the monodose that has just been fractionated in a single apparatus.

Said integrated systems currently available on the market present some drawbacks because they entail an uninterrupted line for distribution of the liquid that goes from the multidose vial to the patient, with the consequence that there may potentially arise an error of operation that involves the administration to a patient of an excessive dose.

Said uninterrupted distribution line moreover necessitates connection, in sequence, of each patient to the multidose vial. In this way, there are potentially risks of contamination between successive patients, given that safety is entirely entrusted to non-return valves positioned along the infusion sets.

Finally, in systems of a known type, the connection of the infusion set (one for each patient) with the multidose vial, is made in open environment in normal hospital surgeries and not in controlled-contamination environments (ventilated hoods, flow hoods, etc.) as recommended by the Standards of Good Preparation Practice in force in the sector. This exposes the multidose vial and the successive patients to risks of microbiological contamination from the surrounding environment.

PURPOSE OF THE INVENTION

A first purpose of the invention is to propose an automatic apparatus for fractionation and infusion of radioactive liquids that will be free from the drawbacks referred to above.

SUMMARY OF THE INVENTION

The above and further purposes and technical advantages have been achieved according to the invention with a device according to at least one of the annexed claims.

The advantages obtained according to the invention lie basically in the fact that the connection between main vial and the infusers is made in a controlled-atmosphere ventilated environment.

Further advantages are represented by the fact that the patient is never in direct contact with the multidose vial and that there are no risks of contamination between patients or risks of overdose.

LIST OF THE DRAWINGS

The above and further advantages will be better understood by any person skilled in the branch from the ensuing description and from the annexed drawings, which are provided purely by way of non-limiting example and in which:

FIG. 4-12A show a sequence of the step of connection of the infusers with the multidose vial within the ventilated chamber of FIG. 3;

FIG. 17 shows a disposable "patient set" usable in the apparatus of the invention;

DETAILED DESCRIPTION

Figure 1:
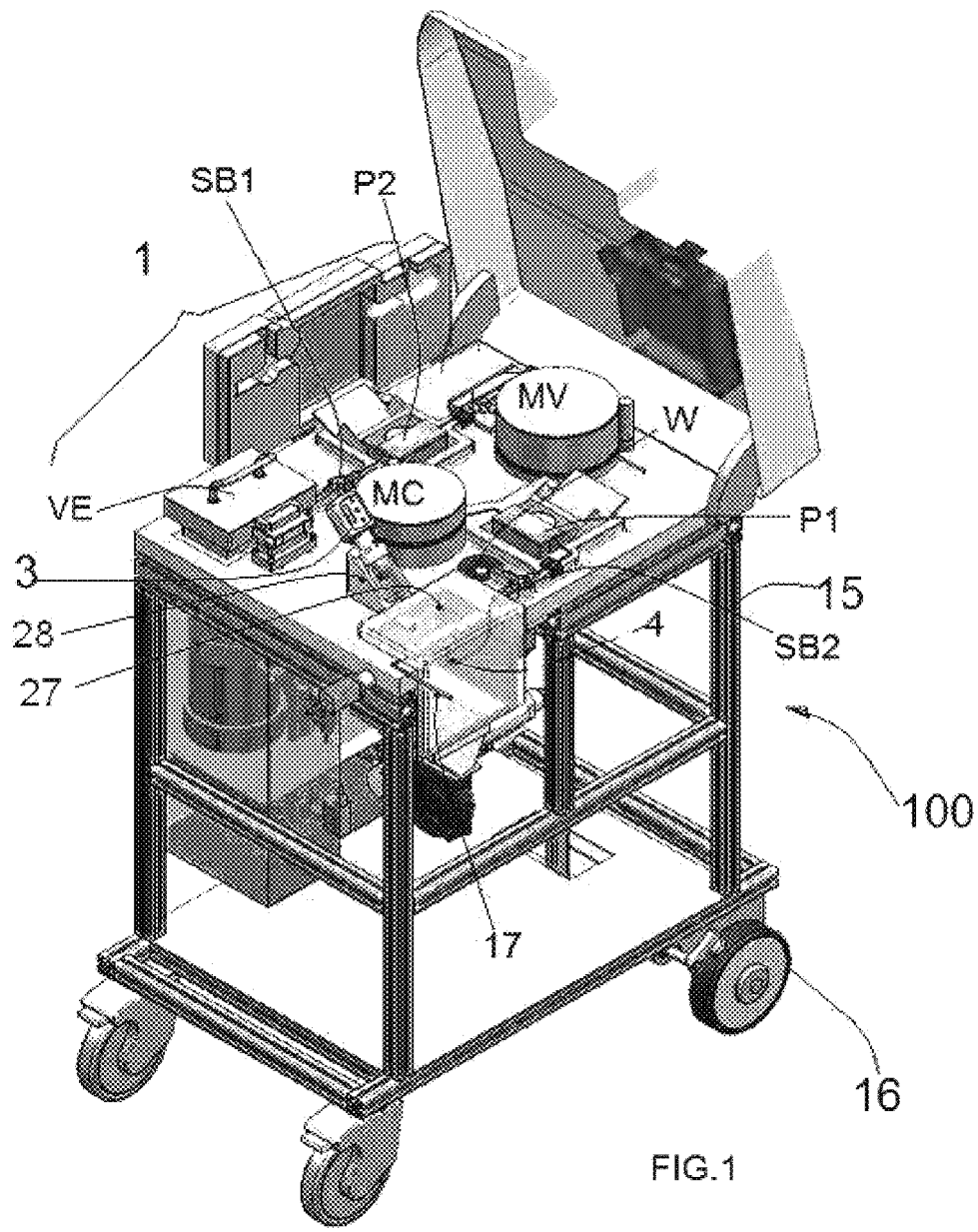
FIG. 1 shows the apparatus of the invention in perspective view.

With reference to the attached drawings, an automatic apparatus is described for fractionation and infusion of radiopharmaceuticals 100, basically comprising a fractionation unit 1 for fractionation into a number of calibrated doses an amount of radioactive liquid contained in a multidose vial VE, and automatic means 2 comprising actuators and tubing for transferring the measured doses delivered by the fractionation unit 1 to a device 3 for administration to a patient S, set in the proximity of the apparatus or in a remote position P.

Preferably, the device 3 is an automatic infuser of the type described in the patent application No. FI2008A000193 filed in the name of the present applicant.

According to the invention, the step of dispensing of the measured dose of liquid to the administration unit 3 is made within a controlled-atmosphere chamber 4 that contains the means for transfer of the doses, and in particular the kit for connection of the administration unit 3 to the fractionating apparatus 1 and the mechanical components that carries out transfer.

Figure 3:
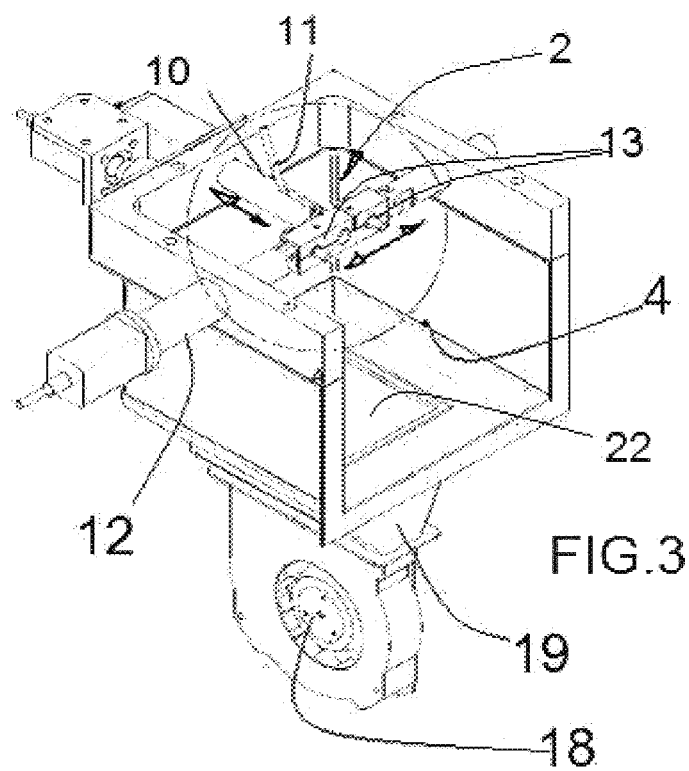
FIG. 3 shows a detail of the ventilated chamber of the apparatus of FIG. 1.

Preferably, the chamber 4 (FIG. 3) is a boxlike body communicating via a duct 19 with a ventilator 18, which ventilates the chamber through an absolute filter 22.

This enables control of the atmosphere present during the critical steps (one for each patient) of disconnection and reconnection of the patient sets from/to the daily set, which is connected to the multidose vial VE, and risks of contagion are prevented in the subsequent administration of doses to different patients.

Figure 15:
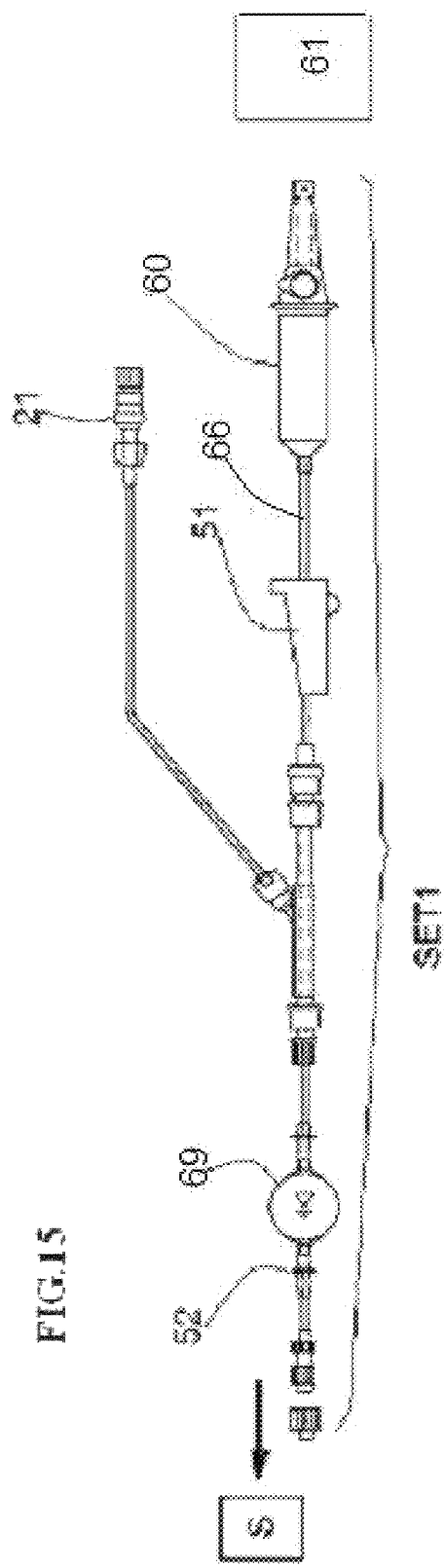
FIG. 15 shows a disposable "infusion set" usable in the apparatus of the invention.
Figure 16:
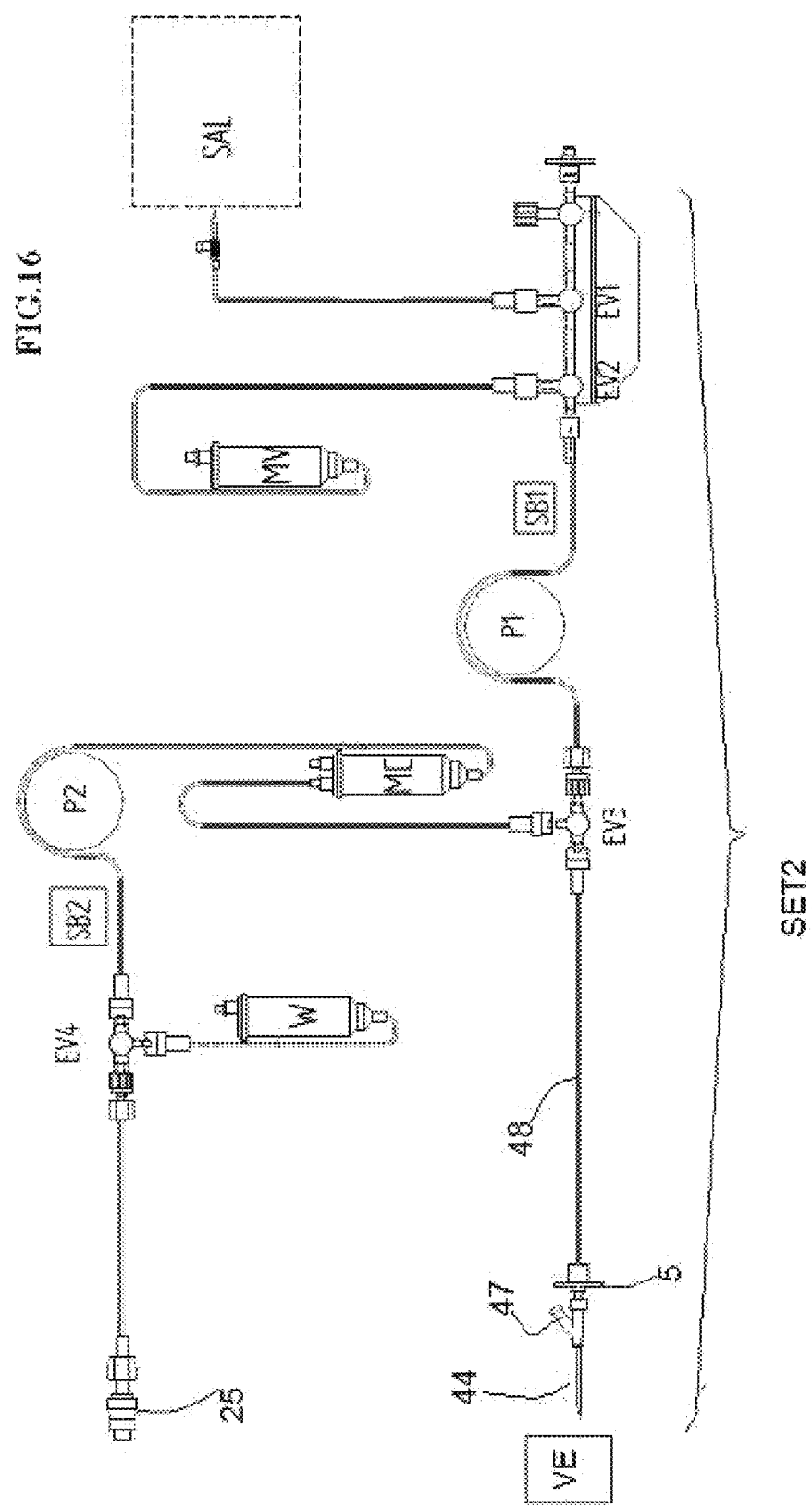
FIG. 16 shows a disposable "daily set" usable in the apparatus of the invention.

With reference to FIGS. 15-17, in the present description:
by "infusion set" is meant an ensemble of disposable tubing SET1 with terminal connections that connect the patient set to the patient and are to be used just once for a single patient.

In the example described, the SET1 comprises a connection 40 to a vial of physiological solution 41, a standard flow regulator (roller) 51 set along a tube 46, a non-return valve 49, and a ventilated filter 52 with the function of separating the possible air bubbles and getting just the liquid to flow to the patient S.

by "daily set" is meant the ensemble of disposable tubing and components SET2 necessary for the fractionation unit 1 for operation during the step of fractionation of the multidose vial into measured doses to be administered, said daily set being designed to used just for a given period, for example one day.

In the case illustrated in FIGS. 16, 16*a*, the SET2 comprises the connection 25, the filter 5, and the stretches of tubes and the connections between the pumps P1, P2, the valves EV1-EV3, the calibrator MC, the vials or containers VE, MV, SAL, W, as described in greater detail hereinafter. FIG. 16*a* shows in particular an embodiment of the SET2 without waste circuit W and comprising a pressure sensor PRO that can be used for a check on integrity of the kit in such a way that, when the pressure does not corresponds to a pre-set pressure, operation thereof can be interrupted, and the kit can be replaced without any risks of losses or malfunctioning. Advantageously, the connection 48 to the needle 44, in this case, is without the venting branch 47, and reintegration of air in the vial VE is carried out with just the needle 44 by means of alternating steps of suction and blowing-in of air.

by "patient set" is meant the ensemble SET3 of disposable tubing and components that can be connected to the daily set and are designed in disposable form for single administration of the radiopharmaceutical to just one patient. In the example described, the patient set comprises at least the plug 23, the line 11, and the syringe 20 of the administering device 3, as described in greater detail hereinafter.

According to an advantageous characteristic of the invention, the aforesaid automatic transfer means 2 comprise mobile connectors that set in communication the administering device 3, through the line 11 of the patient set alternatively with:

the line for arrival of the radioactive liquid (dosed and measured) coming from said multidose vial VE via the connection 25 and the daily set; or the infusion set connected to the connection 21; or else a plug 23 for closing the patient set connected to the administering device 3 already charged with radiopharmaceutical via the connection 25.

Figure 14:
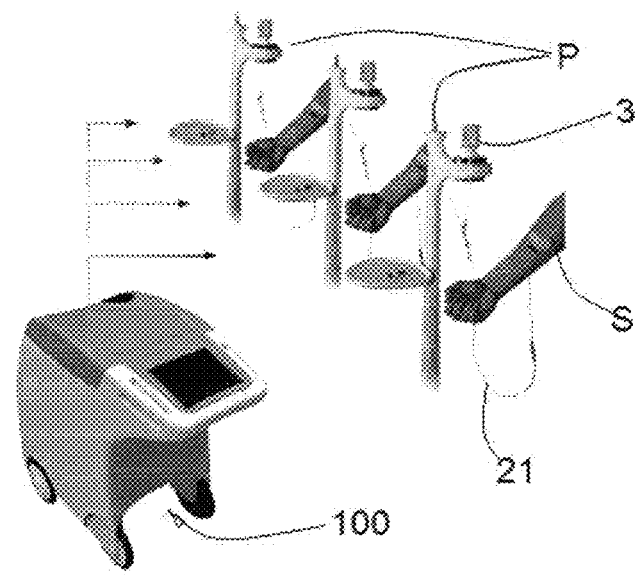
FIG. 14 shows an example of application with administration of the radiopharmaceutical to a patient in remote position with respect to the fractionating unit.

Said administering device 3 is preferably constituted by a shielded automatic infusion device, that may possibly be removed from the chamber 4 and taken to the point of administration P at a distance from the apparatus (FIG. 14).

In this case, connection between the infusion set and the patient set will be made manually by the operator, on the outside of the ventilated chamber 4.

The automatic means 2, after disconnection of the patient set from the daily set, will be limited to screwing the plug on the patient set, previously unscrewed.

Thanks to this solution, direct connection between the patient and the multidose vial is interrupted, and it is guaranteed that each patient is administered the measured dose, without any risk of administering non-controlled doses in the case of malfunctioning of the system.

Moreover, charging of the device 3 with the radiopharmaceutical in controlled environment and use, in combination, of a shielded infusion device enables drastic reduction of the risks of contamination for the operator.

In a preferred embodiment, the transfer means comprise a first mobile arm 10 that carries a connection to the administration line 11 of the patient set, and a second mobile arm 12 carrying the connection 25 to the input line of the radioactive liquid coming from the fractionation unit 1, and at least two seats 13 for housing the connection 21 to the infusion set and the plug 23 of the patient set.

The second arm 12 is mobile in a transverse direction so as to bring in turn the seats 13 alternatively into a position corresponding to the line 11 and enable connection for transfer of liquid.

In turn, the first arm 10 is mobile for displacing the connection to the administration line 11 between the position of connection close to the relevant seat 13 and a detached position of separation.

In the preferred modality of use of the apparatus, administration is performed by removing the unit 3 and taking it to the point of infusion P, as represented schematically in FIG. 14. Advantageously, during administration of the doses to one or more patients S, the apparatus 100 is able to prepare other doses and pre-arrange other units 3 according to the instructions received.

Alternatively, the apparatus 100 can be connected via the connection 21 to a line 17 of the infusion set, communicating with the unit 1 for direct administration of the measured dose from the device 3 to a patient locally connected to the apparatus, without removal of the infuser device from the fractionating machine 1.

Illustrated in FIGS. 4-12A is the succession of the positions occupied by the transfer means during delivery of the doses of liquid to the unit 3, in the case where administration is made subsequently remotely carrying the infuser 3 to the point of administration P.

Figure 4:
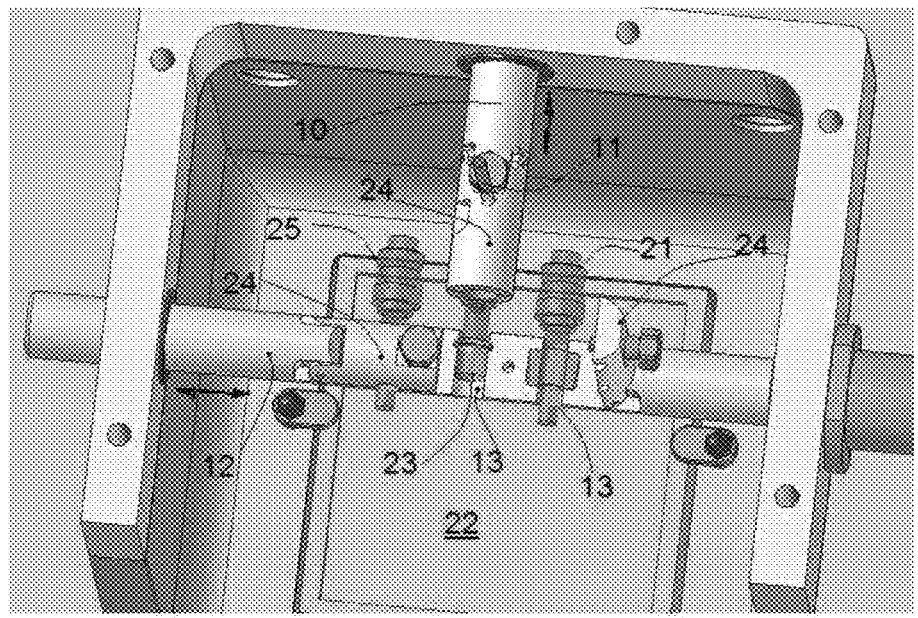
Figure 5:
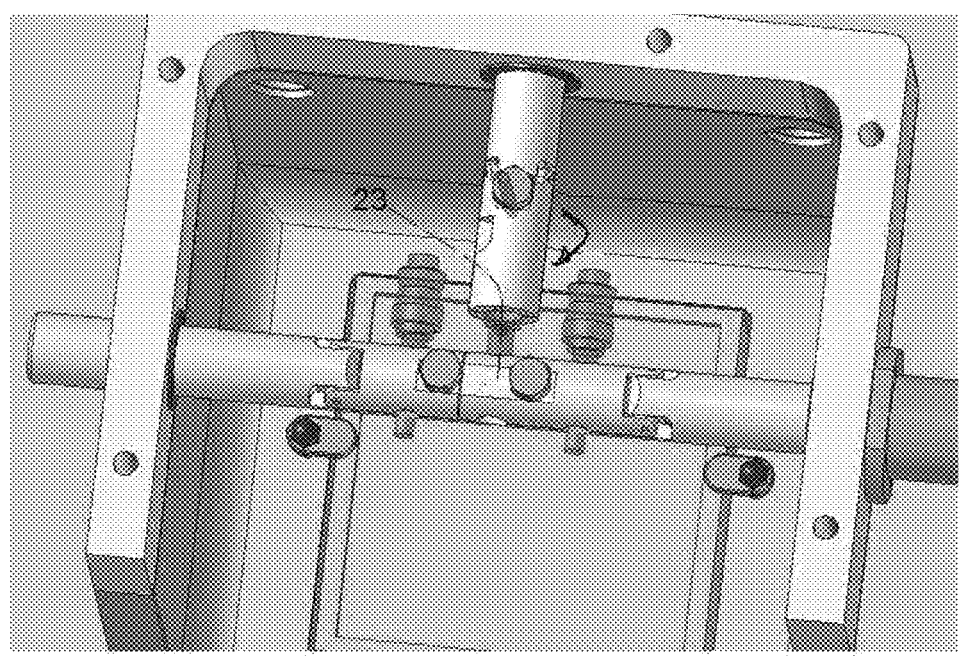

In greater detail, the first step of FIG. 4 is performed with the chamber 4 open.

The operator positions the line 11 in the mobile arm 10, taking care to arrange the terminal plug 23 of the line in the central seat 13 and, in the case of direct administration to the patient, arrange the connection 21 of the infusion set in a different seat 13, for example the outermost seat 13, i.e., the seat furthest to the right in the representation of the figures.

Then the operator clamps the connections with the closing elements 24 and closes the lid of the ventilated chamber 4 in such a way that the ventilator can flush the chamber with filtered air.

After a sufficient time to guarantee proper flushing of the chamber, the device proceeds with the steps of FIGS. 4-12A, automatically.

Figure 6:
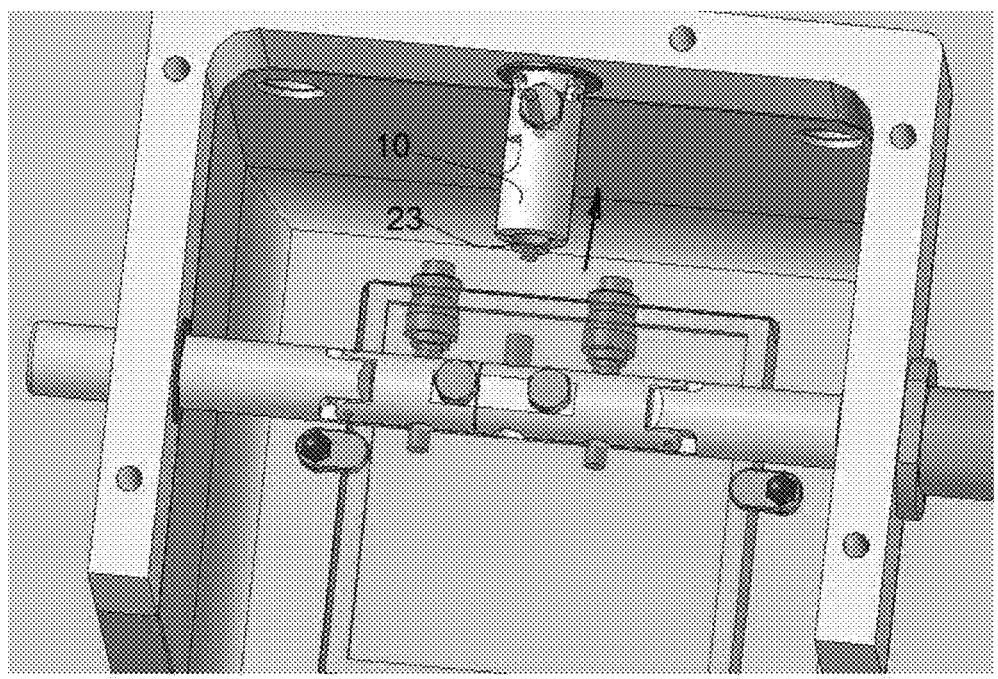
Figure 7:
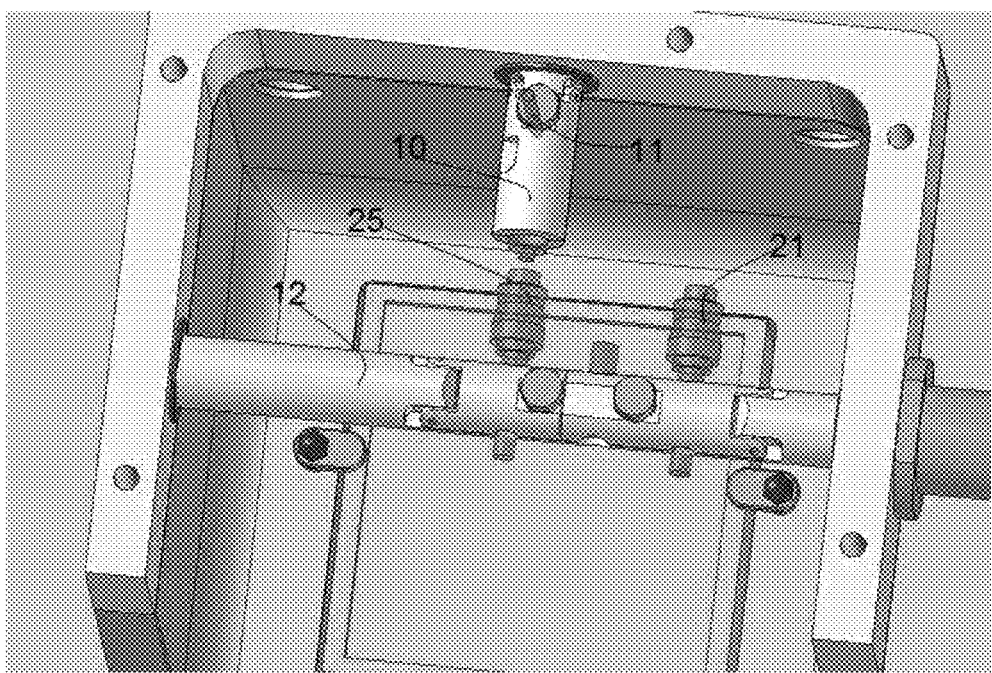

In particular, the arm 10 turns and unscrews the plug of the patient set (FIG. 5), and disengages the line 11 as the arm moves backwards (FIG. 6).

Figure 8:
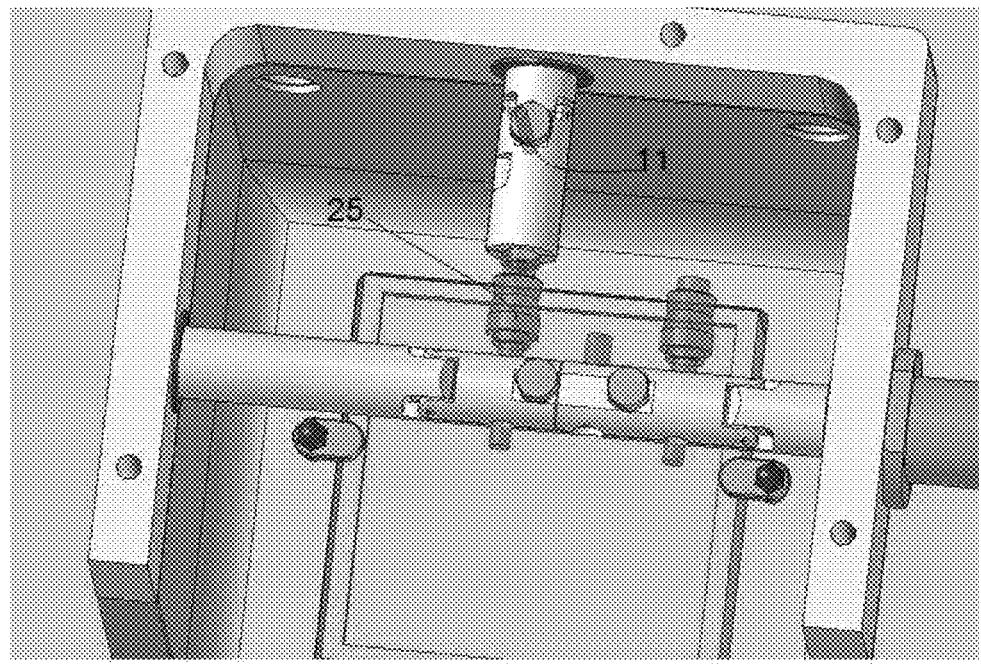
Figure 9:
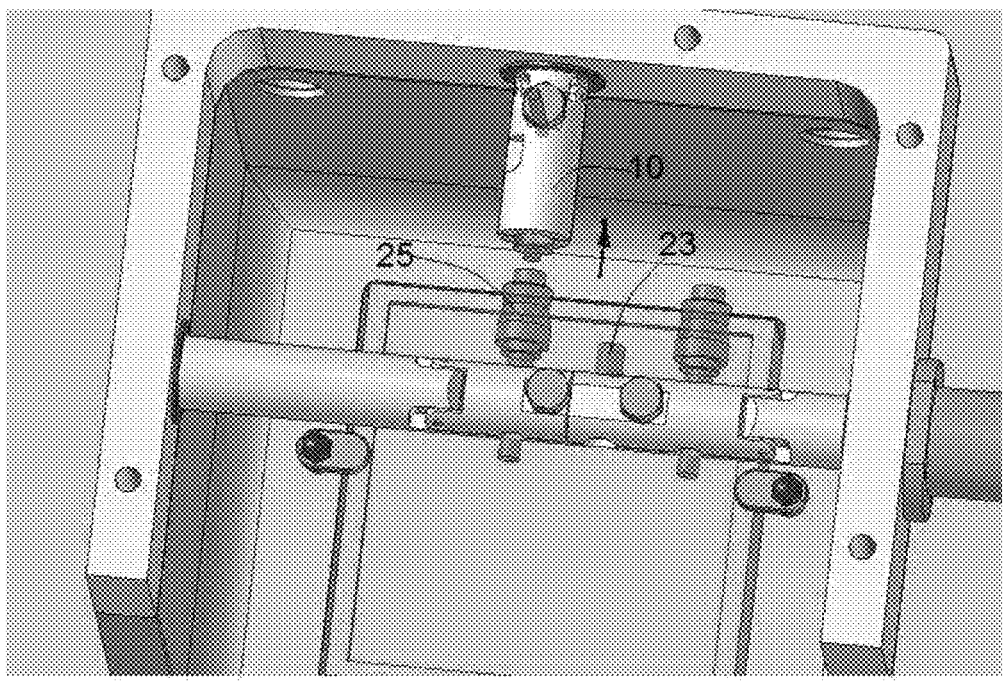
Figure 10A:
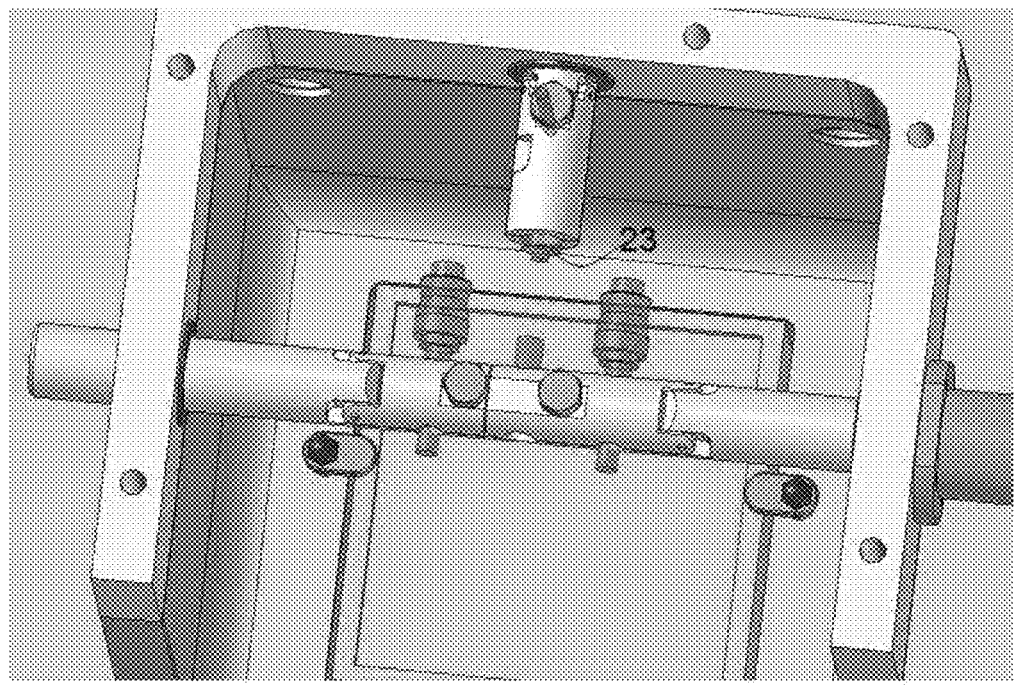
Figure 11A:
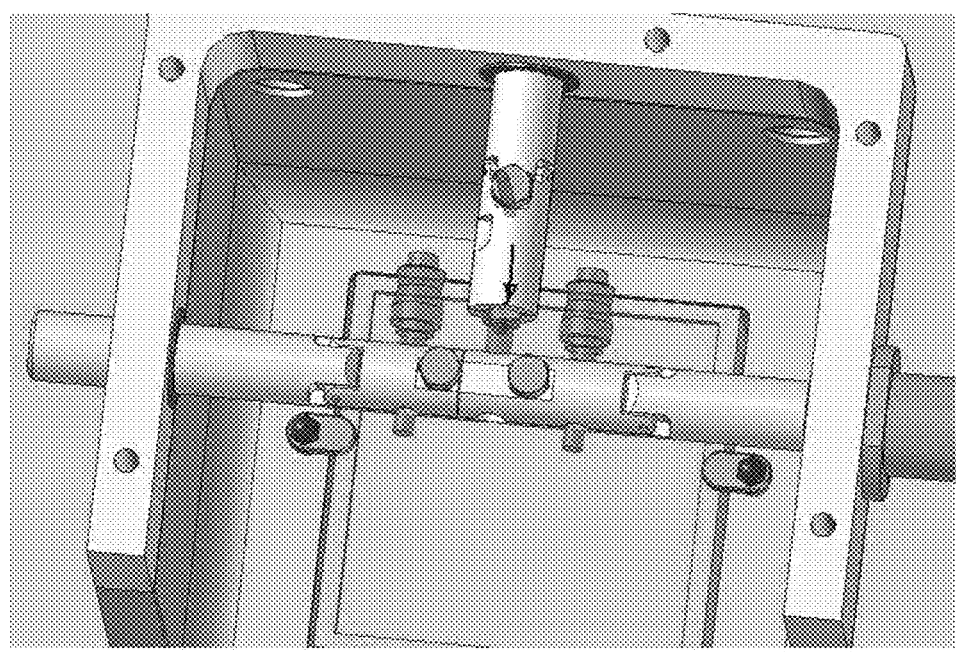
Figure 12A:
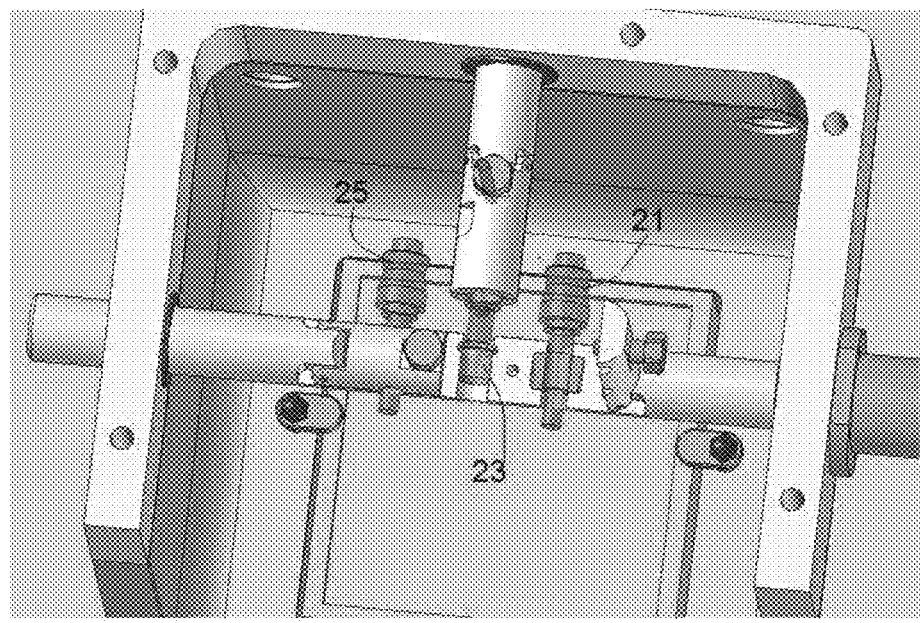
Figure 10B:
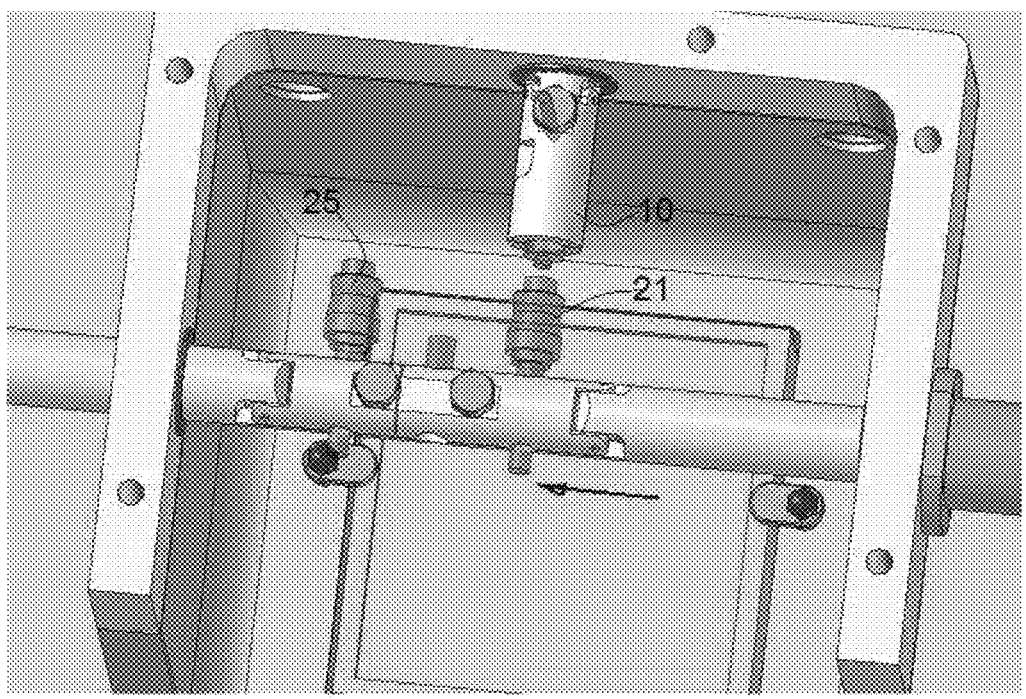
Figure 11B:
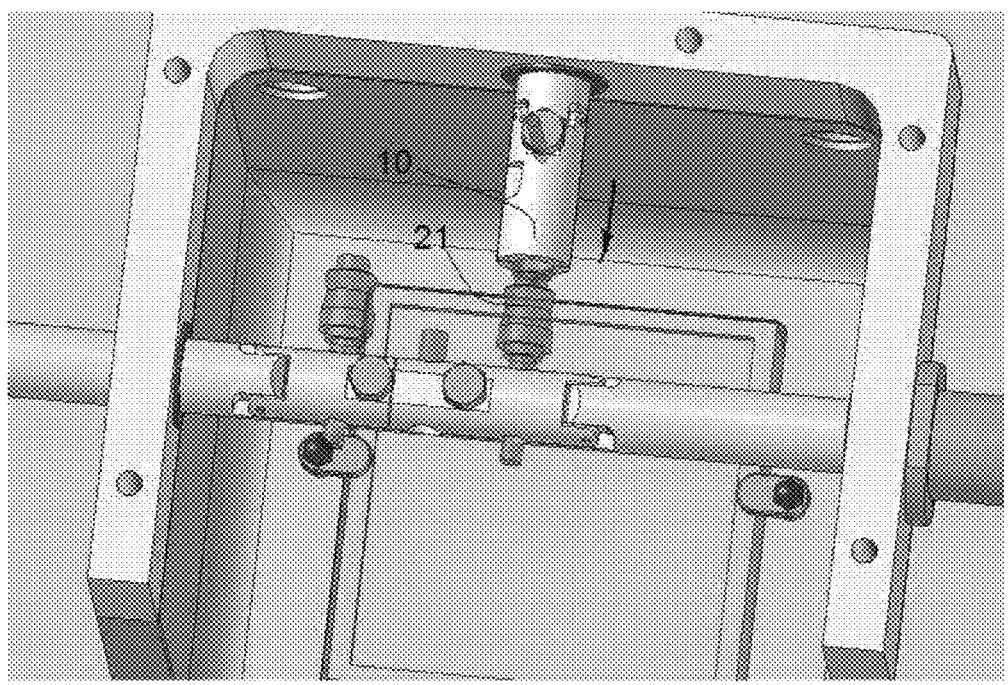

The arm 12 translates and brings the line 11 to the point for connection 25 to the daily set (FIG. 7), and makes the connection of the line 11 to the patient set (FIG. 8).

At this point, the measured dose is transferred from the fractionation unit 1 to the administering device 3.

The system then proceeds in reverse until the plug 23 of the patient set is screwed back on (sequence of FIGS. 9, 10A, 11A, 12A) (preferred mode of operation).

In the case of direct administration, once the administering device 3 has been charged with the dose of radiopharmaceutical, the patient set is then connected to the connection 21 of the infusion set (sequence of FIGS. 9, 10B, 11B), performing a greater translation of the arm 12 (direct-administration mode).

In this case, the device 3 is not removed from its seat 28, and administration is performed locally.

Figure 2:
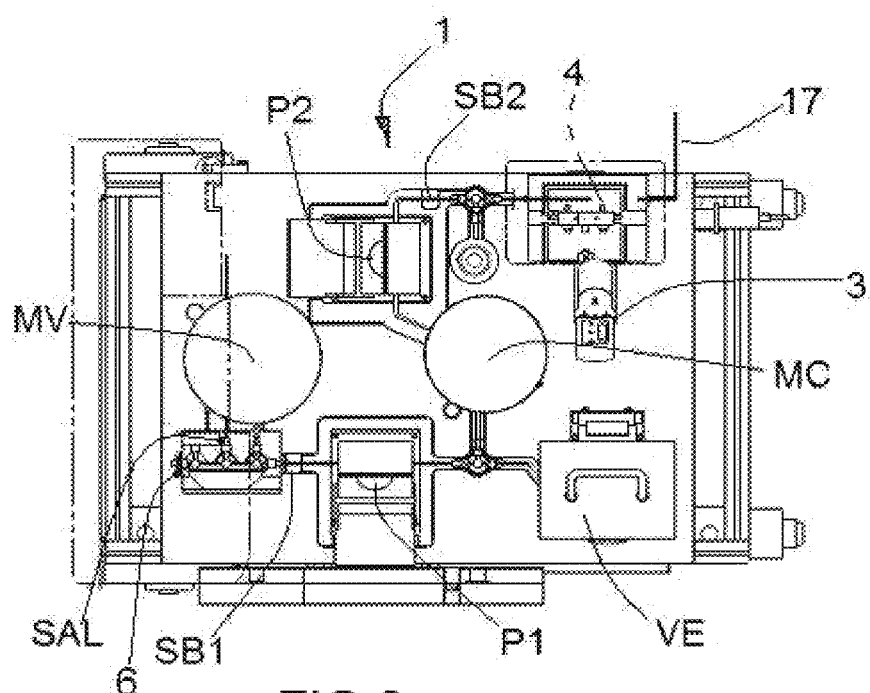
FIG. 2 shows a top plan view of the apparatus of FIG. 1.

Illustrated in FIGS. 1 and 2 is a preferred embodiment of the invention, where the fractionation unit and the transfer means are housed in a transportable structure 15 on wheels 16.

Figure 13:
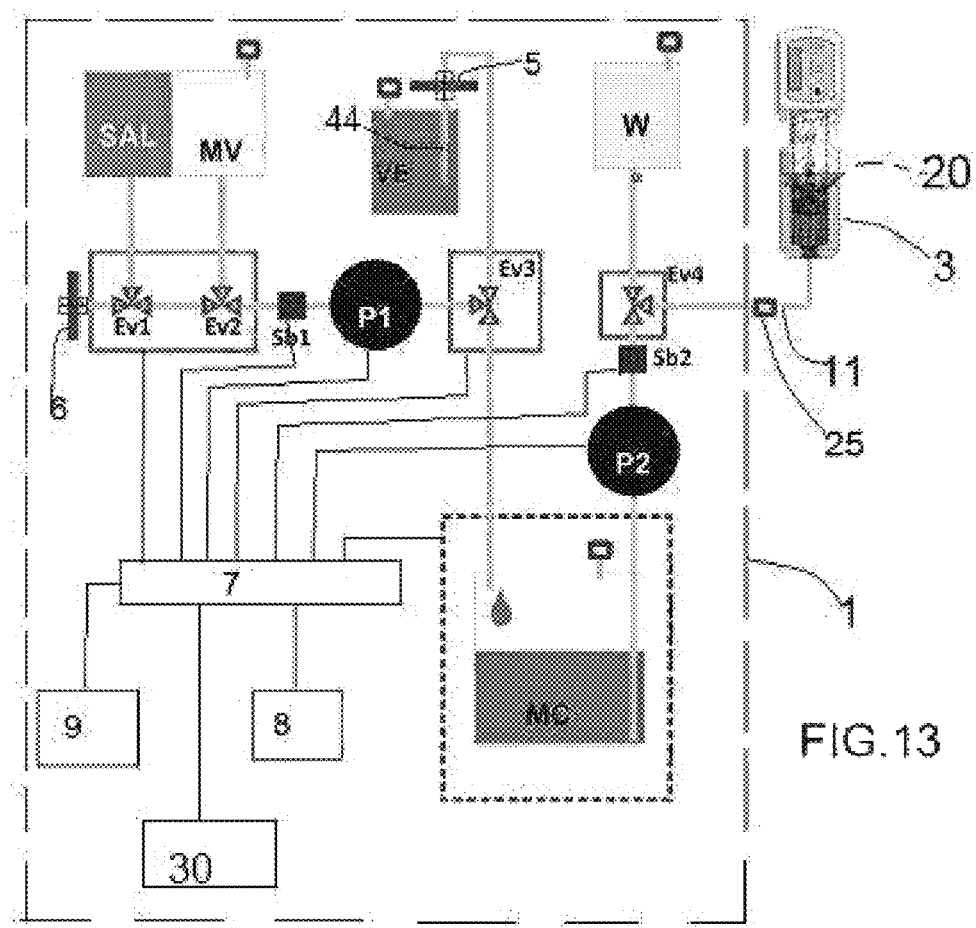
FIG. 13 shows a functional diagram of the apparatus.

In greater detail, and with reference in particular to FIG. 13, in a possible operating scheme, the apparatus comprises a source of physiological saline solution SAL, and an air inlet 6 connected to a first three-way solenoid valve EV1, which is in turn connected to a second three-way solenoid valve EV2, communicating with a main vial MV containing the radioactive liquid to be fractionated.

The valve EV2 is connected at outlet to a first electric pump P1, preferably a peristaltic pump associated to an encoder, connected to a third solenoid valve EV3, which is in turn connected to the multidose vial VE and to a metering container MC via a line 48.

Preferably, moreover provided are filters 5 for in-line sterilization of the radioactive liquid coming from the multidose vial VE.

The container MC is connected at inlet to the valve EV3 and at outlet to a second electric pump P2, similar to the pump P1, which transfers the measured dose of liquid to a fourth solenoid valve EV4, which is in turn connected to the administering device 3 and to a waste discharge 4.

Preferably, the apparatus comprises one or more bubble sensors SB1, SB2 for control of transfer of liquid and recognition of "tube full" operation i.e., operation in the presence of liquid, or "tube empty" operation, i.e., operation with passage of air.

Described in detail hereinafter is a preferred mode of operation, provided as example of use of the apparatus.

Initially, a preliminary verification step is performed to check that the various passageways and the three-way valves are functioning.

In this step:
  EV1 in pos. 2-3, EV2 in pos. 1-3, EV3 in pos. 1-2, and EV4 at rest.
  P1 is activated, draws in saline solution from the vial, and waits for the rising edge of SB1.
  At the edge of SB1, i.e., upon detection of the passage of liquid phase, P1 stops.
  P1 is reactivated and moves a known volume (as per setup) of saline solution up to partial filling MC (volume to transfer to be defined).
  P1 stops, and EV1, EV2, EV3 return to rest
  EV4 in pos. 1-3, and P2 is activated up to the rising edge of SB2
  P2 remains active up to the falling edge of SB2 (passage from liquid to air) and for a time DT such as to empty the line into the waste discharge W
In this step, it is possible to compare the revs of the encoder associated to the pumps P1, P2 counted with SB1 above the threshold with the encoder revs with SB2 above the threshold since the volume of physiological solution that passes through must be the same.

Once functionality of the system has been verified, charging of the multidose vial VE is carried out.

Simultaneously with charging of the multidose vial VE there must also be made the estimation of the total volume transferred. For this reason, the sensor SB1 will be used. In this step:
  EV1 at rest, EV2 in pos. 2-3, EV3 in pos. 1-3, EV4 at rest, P1 is activated and starts charging, and waits for the rising edge of SB1.
  The encoder-rev counter for estimation of the volume is reset, and P1 is reactivated to transfer the radioactive liquid or radiopharmaceutical "RF" into the main vial MV awaiting the falling edge of SB1. The falling edge of SB1 establishes, as a function of the encoder revs counted, the estimation of the total volume.
  P1 remains active for a DT until the line is emptied. Once the radiopharmaceutical RF is transferred into the main vial MV, a step of flushing of the multidose vial starts with the function of cleaning of tubes, filters, and dilution of the concentration of the radiopharmaceutical RF.

In this step:
  EV1 in pos. 2-3, EV2 in pos. 1-3, EV3 in pos. 1-3, EV4 at rest, P1 is activated and transfers the required volume from SAL into VE, whilst, with the rising and falling edges of SB1, it checks whether the amount effectively transferred corresponds to the expected amount.
  Once the volume is reached, EV1 goes into pos. 1-3, and the air filtered by the filter 6 is forced into VE to empty the line.

The steps of filling of the main vial MV and of flushing can be repeated and precede a step of initialization of the kit tubing prearranged for dispensation of the radiopharmaceutical RF.

In this step:
  VE is empty, and the residual activity is minimized;
  MV is full of radiopharmaceutical RF already filtered with the filter 5;
  The lines for transfer of the liquid are empty.
Then
  EV1 at rest, EV2 in pos. 2-3, EV3 in pos. 1-2, EV4 at rest
  P1 is activated and waits for the rising edge of SB1 (the line between MV and SB1 is full), calls back a predefined volume to minimize the RF wasted but at the same time cause the edge of the liquid to remain in any case to the right, beyond EV2, towards the MC.
  EV1 in pos. 2-3, EV2 in pos. 1-3, EV3 in pos. 1-2, EV4 at rest. P1 is activated for a pre-set volume so as to force the small amount of RF present beyond EV2 into MC and at the same time fill the entire line up to MC with saline solution, to be able to work in "tubes full" mode.
  At the end of transfer of saline solution, so as to bring the portion of RF and a small amount of saline solution into MC, P1 recovers turning in a counterclockwise direction so as to remove any possible drops present at the head of the MC.
  EV1, EV2, EV3 at rest and EV4 in pos. 1-3. P2 is activated and transfers the entire contents of MC in W up to the rising edge of SB2. P2 remains active for a DT until the line is completely emptied (with SB2 a check is made to see whether the tube is actually empty; otherwise, the DT is reset automatically).

With W full, flushing of MC is carried out in order to minimize the background effect in the subsequent measurements of activity by MC.

In this step,
  EV1 in pos. 2-3, EV2 in pos. 1-3, EV3 in pos. 1-2, EV4 at rest. P1 is activated for a pre-set volume to be transferred into MC.
  EV1, EV2, EV3, EV4 at rest and EV4 in pos. 1-3. P2 is activated and transfers the entire contents of MC in W up to the rising edge of SB2. P2 remains active for a DT until the line is completely emptied (with SB2 a check is made to see whether the tube is actually empty; otherwise, the DT is reset automatically).

At this point, it is possible to carry out dispensation of RF and of saline solution in MC for the doses envisaged.

Dispensation of RF: EV1 at rest, EV2 in pos. 2-3, EV3 in pos. 1-2, EV4 at rest, P1 is activated to take in the required volume.

Transfer with saline solution: EV1 in pos. 2-3, EV2 in pos. 1-3, EV3 in pos. 1-2, EV4 at rest. P1 is activated for a pre-set volume so as to force the RF present beyond EV2 in MC and at the same time fill all the line up to MC with saline solution.

Once fractionation is through, if the activity read in the MC is correct, the dose is then transferred into the syringe:

EV1, EV2, EV3, EV4 in pos. 1-3. P2 is activated and waits for the rising edge of SB2 and stops (in the meantime the air is disposed of in W)

EV1, EV2, EV3, EV4 in pos. 2-3, P2 is activated, transfers the entire contents of MC into the administration unit 3, up to the falling edge of SB2.

P2 remains active for a DT until the line that goes from SB2 to the unit 3 is completely emptied.

Preferably, the fractionation and dispensation cycle terminates with a step of flushing of the calibrator MC to minimize residual activity.

The operation just described is executed automatically by means of a programmable electronic unit 7 interfaced to a data-exchange unit 8, for example for remote control and/or updating of the programming software, and to a control panel, for example a touch screen.

The invention achieves important advantages, in particular for the aseptic conditions guaranteed by the controlled-atmosphere chamber 4 in the steps of replacement of the "disposable" sets, i.e., of the disposable parts that must be changed in the subsequent administrations to the patient and in the steps of filling of the multidose vials to be fractionated.

Furthermore, the use of connection means, whether automatic or not, which connect alternatively to the fractionation unit and to the administration lines guarantee that there is no direct connection between the patient and the multidose vial.

Figure 18:
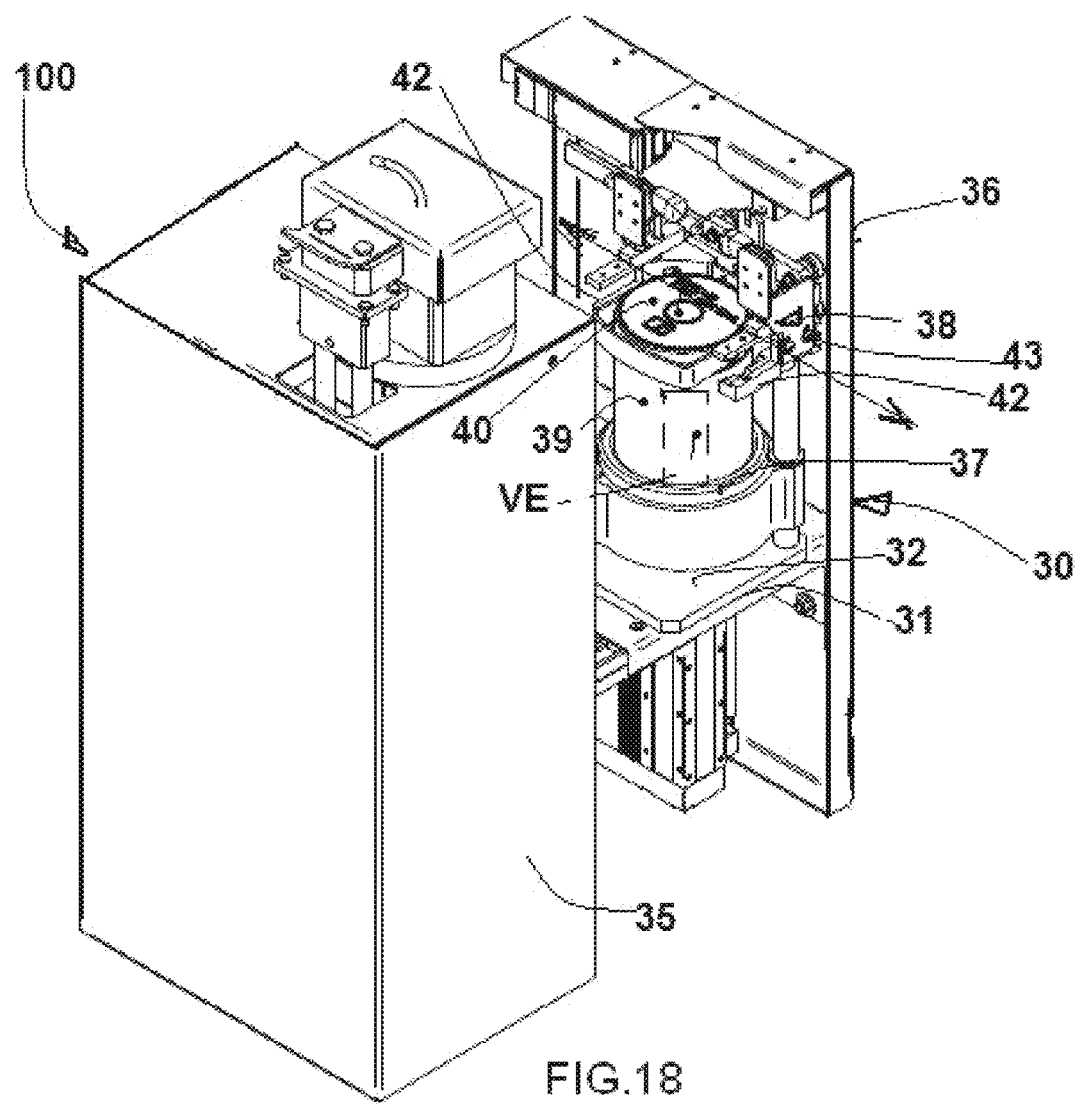
FIG. 18 shows a preferred embodiment of an apparatus according to the invention provided with a device for automatic change of the external vial.
Figure 19B:
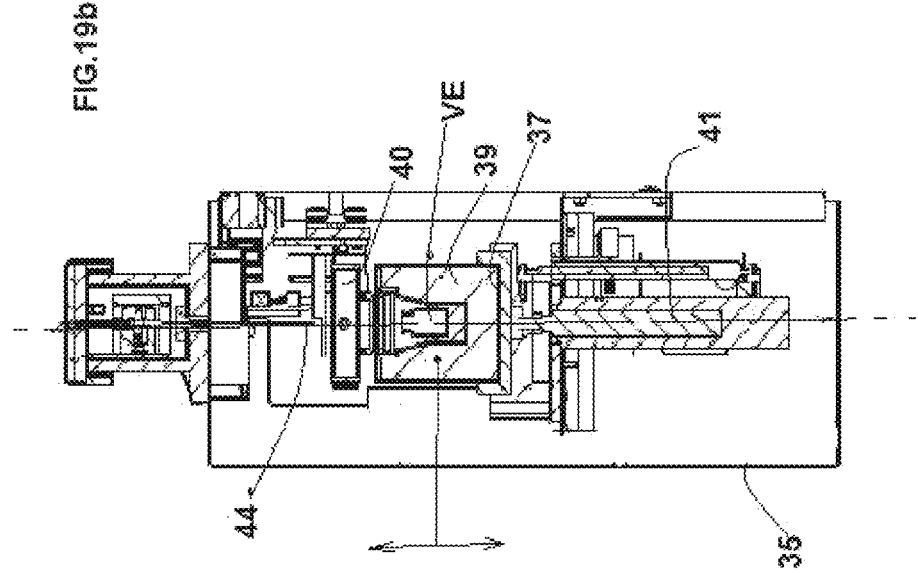
FIGS. 19a and 19b show a cross section of the apparatus of FIG. 18 in the configuration of extraction and the configuration of concealment, respectively, of the device for automatic vial change.
Figure 19A:
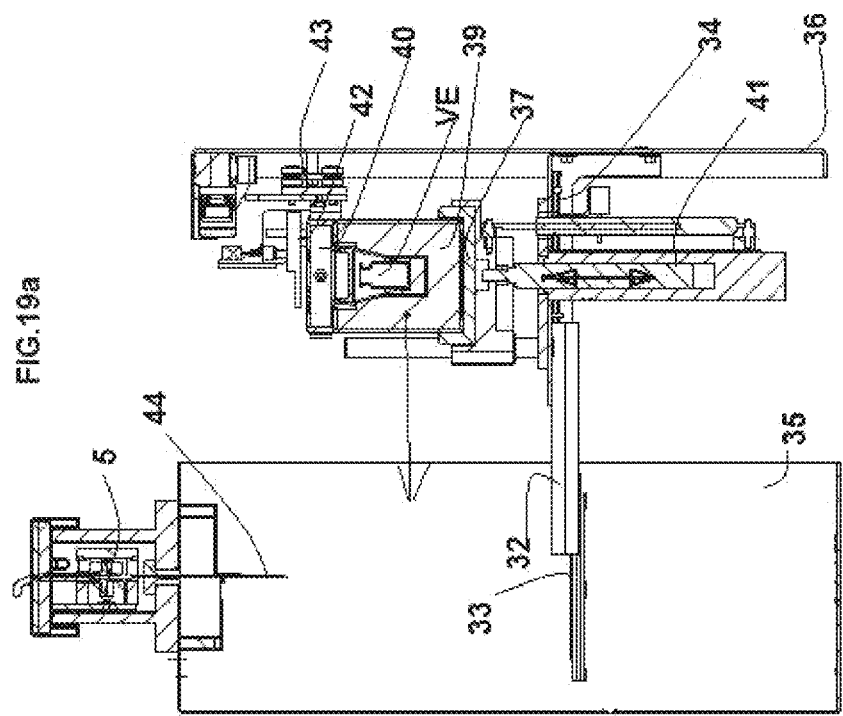

With reference to FIGS. 18 and 19, an apparatus 100 according to the invention is described provided with a device 30 for automatic connection to a new external multidose vial VE.

The device 30 is mounted on an extractable carriage 31 that can be concealed within the outer casing of the apparatus 100.

Preferably, the carriage 31 is mobile thanks to slidable plates 32 mounted on linear guides 33 and 34, which are mounted, respectively, on the casing 35 of the apparatus 100 and in cantilever fashion on a front side 36 of the device, but it is understood that different mechanical solutions may be adopted.

The device 30 further comprises a vertically mobile seat 37 shaped for stable resting of a shielded container capable of housing the vial VE to be connected and provided with a shielded plug 40.

On top of the seat 37 the device 30 is provided with a mechanism 38 for gripping and translation of the plug, capable of performing a movement of lateral translation of the plug 40 to expose the body 39 and hence the vial VE contained therein.

Preferably, the seat 37 is carried by an underlying pneumatic cylinder 41 that bestows the vertical motion on the container 39, whilst the transverse movement is bestowed on the plug 40 by the gripping mechanism 38 comprising opposed elements 42 that can be closed like a vice and mounted on transverse linear guides 43 mounted on the front 36.

In operation, the container 39 with the vial VE inside it is manually housed in the seat 37 when the device 30 is in the extracted configuration (FIG. 19A), and the plug 40 is released from vertical engagement with the container, for example, by being unscrewed it if it is of the screw type. Now, the operator is protected from exposure because the shielded plug remains as cover for the vial VE.

From this moment an automatic procedure starts in the absence of operator controlled by the control unit 7 and by appropriate motor drives of the mobile parts, not shown for simplicity of representation.

In the procedure of vial change, the carriage 31 goes back into the casing 35 in a concealed way (FIG. 19b), the elements 42 approach the two sides of the plug 40, grip it, and translate simultaneously on the guides 43 displacing the plug 40 and freeing access to the vial VE from above.

In the concealed configuration of the device 30 (FIG. 19B) the carriage has gone completely back in, and the vial VE is aligned underneath a needle 44 that constitutes the start of the line of the radioactive liquid to be fractionated coming form the multidose vial VE.

To start transfer of the liquid it will consequently be sufficient for the cylinder 41 to lift the seat 37 until the needle 44 enters the vial VE and is introduced into the liquid contained therein.

Preferably, it is envisaged that the operation of lifting the seat 37 is controlled precisely in amplitude to enable the bottom of the vial to be reached automatically.

For this purpose, a pressure sensor is also provided that detects the peak pressure undergone by the needle 44, and the movement of the cylinder 41 is subject to a control of pressure on the needle 44, in such a way that at the moment of contact between the needle 44 and the bottom of the vial VE the movement of the latter is blocked, to protect the needle 44, which consequently will come to occupy a position where it is has a maximum capacity of suction from inside the vial VE.

The present invention has been described according to preferred embodiments but equivalent variants may be devised, without departing from the scope of the invention.

The invention claimed is:

1. An apparatus for fractionation and infusion of radiopharmaceuticals to a patient, comprising:
    a fractionation unit configured to fractionate into a number of calibrated doses an amount of radioactive liquid contained in a multidose vial, the fractionation unit comprising:
        a multidose vial,
        an administration device configured to administer at least one of said doses to the patient,
        a controlled atmosphere chamber, and
        a line in communication with said administration device,
    means comprising actuators and tubing for transferring in succession said doses from the multidose vial to said administration device;
    one or more connections configured to set said fractionation unit in communication with said administration device; and
    contained within the controlled-atmosphere chamber, one or more connectors and lines configured to connect said one or more connections to said line in communication with said administration device.

2. The apparatus according to claim 1, wherein said controlled-atmosphere chamber is a ventilated chamber.

3. The apparatus according to claim 2, wherein said administration device is a shielded device, which can be removed from connection with said one or more connections in said chamber and can be carried to a position of administration set at a distance from the apparatus, and said one or more connectors and lines comprise mobile connectors, which can be actuated automatically and set the administration device in communication, through the line, alternatively:

with a connection to a line for arrival of a dosed and metered radioactive liquid coming from said multidose vial; or with a plug of the line in communication with said administration device.

4. The apparatus according to claim 2, wherein said one or more connectors and lines comprise mobile connectors, which can be actuated automatically and set the administration device in communication, through the line, alternatively:

with a connection to the line for arrival of a dosed and metered radioactive liquid coming from said multidose vial; or with a connection to an infusion set connected to said administration device and designed for administering directly a dose to the patient.

5. The apparatus according to claim 1, wherein said administration device is a shielded device, which can be removed from connection with said one or more connections in said controlled-atmosphere chamber and can be carried to a position of administration set at a distance from the apparatus, and said one or more connectors and lines comprise mobile connectors, which can be actuated automatically and set the administration device in communication, through the line with a connection to a line for arrival of dosed and metered radioactive liquid coming from said multidose vial; or with a plug of the line in communication with the administration device.

6. The apparatus according to claim 5, wherein said mobile connectors comprise:

a first mobile arm carrying a connection to said line in communication with said administration device for transfer of the radioactive liquid to said administration device; and a second mobile arm provided with at least two seats for housing the connection to said line and a connection to an infusion set provided for the patient and/or said plug, wherein said second arm is mobile for bringing at least two of said seats alternatively into a position for connection with said line in communication with said administration device, and said first mobile arm is mobile for displacing said connection to the line between a position of connection close to said seats and a detached position of separation.

7. The apparatus according to claim 5, wherein said one or more connectors and lines comprise mobile connectors, which can be actuated automatically and set the administration device in communication, through the line, alternatively:

with a connection to a line for arrival of the dosed and metered radioactive liquid coming from said multidose vial; or with a connection to an infusion set connected to said administration device and designed for administering directly a dose to the patient, wherein the patient is part of a number of patients.

8. The apparatus according to claim 1, wherein said one or more connectors and lines comprise mobile connectors, which can be actuated automatically and set the administration device in communication, through a line with a connection to a line for arrival of a dosed and metered radioactive liquid coming from said multidose vial; or with a connection to an infusion set connected to said administration device and designed for administering directly a dose the patient.

9. The apparatus according to claim 8, wherein said mobile connectors comprise:

a first mobile arm carrying a connection to the line in communication with said administration device for transfer of the radioactive liquid to said administration device; and a second mobile arm provided with at least two seats for housing a connection to said line and a connection to an infusion set provided for the patient and/or a plug, wherein said second arm is mobile for bringing at least two of said seats alternatively into a position for connection with said line in communication with said administration device, and said first mobile arm is mobile for displacing said connection to the line between a position of connection close to said seats and a detached position of separation.

10. The apparatus according to claim 1, comprising filters positioned for in-line sterilization of the radioactive liquid coming from the multidose vial.

11. The apparatus according to claim 1, comprising a metering container positioned for in-line metering of the activity of the radioactive liquid transferred to the administration device.

12. The apparatus according to claim 1, further comprising:

a source of physiological solution;

a main vial;

a first three-way solenoid valve connected to an air inlet, to said source of physiological solution, and to a second three-way solenoid valve connected to said main vial;

a first electric pump connected to said second valve and to a third solenoid valve, which is in turn connected to said multidose vial and to a metering container; and a second electric pump connected to said metering container and to a fourth solenoid valve, which can be in turn connected via a connection point to said administration device and to a waste discharge.

13. The apparatus according to claim 12, further comprising a control unit for automatic management of said solenoid valves and said pumps in response to instructions coming from a data-exchange unit.

14. The apparatus according to claim 1, further comprising one or more bubble sensors positioned for controlling transfer of liquid.

15. The apparatus according to claim 1, further comprising a control touch-screen.

16. The apparatus according to claim 1, further comprising a needle configured to be inserted in the multidose vial, said needle being without venting branches, reintegration of air into the vial being carried out by means of alternating steps of suction and blowing-in of air through the needle alone.

17. The apparatus according to claim 16, further comprising a device configured for automatic connection of the apparatus to an inlet line for the radioactive liquid contained in the multidose vial set within a shielded container provided with a shielded plug, the device comprising:

first means of movement of the container configured for extraction and concealed insertion of said container from/into an outer casing of the apparatus;

means for movement of the plug configured for removing the plug from the container and freeing access to the multidose vial from the outside of the shielded container; and means for mutual movement of the container and of the needle configured for inserting said needle into said multidose vial in a controlled way.

18. The apparatus according to claim 17, wherein said means for mutual movement of the container and of the needle comprise a pressure sensor that detects a peak pressure undergone by the needle in such a way that at a moment of contact between the needle and the multidose vial, the mutual movement is blocked with the needle in a position where the needle has a maximum capacity of suction from inside the multidose vial.

19. The apparatus according to claim 1,
wherein the controlled-atmosphere chamber is in communication via a duct with a ventilator, which ventilates the chamber.

\* \* \* \* \*